US010933416B2

(12) United States Patent
Croquette et al.

(10) Patent No.: US 10,933,416 B2
(45) Date of Patent: Mar. 2, 2021

(54) DEVICE FOR THE ANALYSIS OF NUCLEIC ACID MOLECULES

(71) Applicants: Paris Sciences Et Lettres—Quartier Latin, Paris (FR); Centre National de la Recherche Scientifique (CNRS), Paris (FR); Universite Paris Diderot Paris 7, Paris (FR); Sorbonne Universite, Paris (FR)

(72) Inventors: Vincent Croquette, Antony (FR); David Bensimon, Paris (FR); Jimmy Ouellet, Lardy (FR); Jean-François Allemand, Bourg la Reine (FR); Charles Andre, Paris (FR); Gordon Hamilton, Paris (FR)

(73) Assignees: Paris Sciences Et Lettres—Quartier Latin; Centre National de la Recherche Scientifique (CNRS); Universite Paris Diderot Paris 7; Sorbonne Universite

( * ) Notice: Subject to any disclaimer, the term of this patent is extended or adjusted under 35 U.S.C. 154(b) by 0 days.

(21) Appl. No.: 15/571,679

(22) PCT Filed: May 6, 2016

(86) PCT No.: PCT/EP2016/060155
§ 371 (c)(1),
(2) Date: Nov. 3, 2017

(87) PCT Pub. No.: WO2016/177869
PCT Pub. Date: Nov. 10, 2016

(65) Prior Publication Data
US 2018/0361378 A1    Dec. 20, 2018

(30) Foreign Application Priority Data

May 7, 2015 (EP) .................................... 15305710

(51) Int. Cl.
*C12Q 1/68* (2018.01)
*B01L 3/00* (2006.01)
(Continued)

(52) U.S. Cl.
CPC ........ *B01L 3/50273* (2013.01); *C12Q 1/6825* (2013.01); *G01N 27/3275* (2013.01);
(Continued)

(58) Field of Classification Search
CPC ........ C12Q 2563/113; C12Q 2563/116; C12Q 2565/607; C12Q 2563/143; C12Q 1/6816;
(Continued)

(56) References Cited

U.S. PATENT DOCUMENTS 6,133,436 A    10/2000  Koster et al.
2003/0027187 A1   2/2003  Strick et al.
(Continued)

FOREIGN PATENT DOCUMENTS

EP    2390350 A1   11/2011
EP    2390351 A1   11/2011
(Continued)

OTHER PUBLICATIONS

Davenport, et al., The Role of Pore Geometry in Single Nanoparticle Detection, ACS Nano, Sep. 25, 2012, pp. 8366-8380, vol. 6, No. 9.
(Continued)

*Primary Examiner* — Betty J Forman
(74) *Attorney, Agent, or Firm* — Lerner, David, Littenberg, Krumholz & Mentlik, LLP (57) ABSTRACT

The invention proposes a device for analyzing nucleic acid molecules (M), comprising: —a bead (20), on which one molecule can be anchored at one end, —a surface (520), on which the molecule can be anchored at the other end, —an actuator (30), adapted to cause the bead to move relative to said surface in one direction, —a sensor (50), adapted to
(Continued)

measure a distance between the bead and the surface, the device further comprising a well (11), having an axis (X-X) extending along the direction of motion of the bead and a bottom (110) formed by said surface, said well being filled with electrically conductive solution (40), and receiving the bead, the sensor being adapted to measure an impedance of the well, depending on a distance between the bead and the surface, to determine, the distance between the bead and the surface.

18 Claims, 6 Drawing Sheets

(51) Int. Cl.
  *C12Q 1/6825* (2018.01)
  *G01N 27/327* (2006.01)
  *G01N 27/07* (2006.01)

(52) U.S. Cl.
  CPC ..... *B01L 3/5085* (2013.01); *B01L 2200/0668* (2013.01); *B01L 2300/0627* (2013.01); *B01L 2300/0829* (2013.01); *B01L 2400/043* (2013.01); *B01L 2400/0436* (2013.01); *C12Q 2523/307* (2013.01); *C12Q 2525/301* (2013.01); *C12Q 2563/116* (2013.01); *C12Q 2563/155* (2013.01); *G01N 27/07* (2013.01)

(58) Field of Classification Search
  CPC ............ C12Q 1/6825; C12Q 2523/303; G01N 27/227; G01N 27/3278; G01N 27/745; G01N 27/02; G01N 27/3275
  See application file for complete search history.

(56) References Cited

U.S. PATENT DOCUMENTS

| 2005/0112544 | A1* | 5/2005 | Xu ........................ C12M 23/12 435/4 |
| 2008/0286878 | A1* | 11/2008 | Vezenov ................ B82Y 35/00 436/94 |
| 2010/0035252 | A1* | 2/2010 | Rothberg ............. C12Q 1/6874 435/6.12 |
| 2010/0075340 | A1 | 3/2010 | Javanmard et al. |
| 2010/0267169 | A1 | 10/2010 | Hajimiri et al. |
| 2012/0149129 | A1* | 6/2012 | Pai ...................... G01N 27/3278 436/501 |
| 2013/0034880 | A1* | 2/2013 | Oldham ............ B01L 3/502738 435/91.5 |
| 2014/0323330 | A1* | 10/2014 | Bergo .............. G01N 33/54306 506/9 |
| 2015/0065353 | A1* | 3/2015 | Turner ................. G01N 27/227 506/2 |

FOREIGN PATENT DOCUMENTS

| WO | 2011147929 A1 | 12/2011 |
| WO | 2011147931 A1 | 12/2011 |
| WO | 2013093005 A1 | 6/2013 |
| WO | 2014114687 A1 | 7/2014 |

OTHER PUBLICATIONS

Ding, et al, On-Chip Manipulation of single microparticles, cells, and organisms using surface acoustic waves, PNAS, Jul. 10, 2012, pp. 11106-11109, vol. 109, No. 28.

Ding, et al., "Single-molecule mechanical identification and sequencing", Nature Methods, Apr. 1, 2012, vol. 9, No. 4, pp. 367-372.

Extended European Search Report for Application No. EP15305710.4 dated Dec. 8, 2015.

Hunter, et al, High-affinity monoclonal antibodies to the cardiac glycoside, digoxin, Journal of Immunology, Sep. 1982, pp. 1165-1172, vol. 129, No. 3.

International Search Report from Application No. PCT/EP2016/060155, dated Sep. 23, 2016.

Manosas, et al., "Coupling DNA unwinding activity with primer synthesis in the bacteriophage T4 primosome", Nature Chemical Biology, Dec. 1, 2009, pp. 904-912, vol. 5, No. 12.

Sitters, et al, Acoustic Force spectroscopy, Nature Methods, Jan. 2015, pp. 47-53, vol. 12, No. 1.

Smith, et al., "Direct Mechanical Measurements Of The Elasticity of Single DNA Molecules By Using Magnetic Beads", Nature, Nov. 13, 1992 , pp. 1122-1126, vol. 258, Nature Publishing Group, United Kingdom.

Xiong, et al., Electrophoretic mobility measurement by laser Doppler velocimetry and capillary electrophoresis of micrometric fluorescent polystyrene beads, Analytical Methods, 2012, 4, 183.

* cited by examiner

Gradient of magnetic field in microtweezers

FIG. 6

DEVICE FOR THE ANALYSIS OF NUCLEIC ACID MOLECULES

CROSS REFERENCE TO RELATED APPLICATIONS

The present application is a national phase entry under 35 U.S.C. § 371 of International Application No. PCT/EP2016/060155 filed May 6, 2016, which claims priority from European Patent Application No. 15305710.4 filed May 7, 2015, the disclosures of which are incorporated herein by reference.

TECHNICAL FIELD OF THE INVENTION

The invention relates to a device and a process for analyzing molecules. The invention applies in particular to the analysis of nucleic acid molecules such as DNA or RNA.

BACKGROUND ART

If nucleic acid molecules are attached to micro-scale beads, information about the nucleic acid structure can be inferred by manipulating the beads and tracking their position with high resolution. Under particular experimental conditions, tracking the location of the bead in real time can be used to generate useful information about the structure of the DNA or RNA molecule to which it is attached.

This can, in turn, be used to determine the molecule's gross organization, base sequence, the presence of biochemical modifications to the nucleic acid bases, and the interactions of the molecule with proteins such as polymerases, helicases, topoisomerases, etc.

A device for performing such analysis of nucleic acid molecules has been described in document US 2003/0027187. This device comprises optical means to determine the position of the beads attached to the molecule.

More specifically, beads are illuminated from above and viewed through a microscope objective via an image captured on an HD video camera. The position of a bead is followed in real time by a tracking algorithm measuring x and y coordinates from the bead image, whereas the determination of the z-position, that is, the height of the bead with reference to the surface to which the molecule is attached, is determined thanks to light diffraction patterns surrounding the image of the bead.

Indeed, the light illuminating the bead is scattered from the bead and creates a diffraction pattern by interfering with the direct illumination light in order to use this diffraction pattern to infer the z-position of the bead, a set of images of the diffraction pattern is acquired at various distances from the focal point of the objective by keeping the bead in a fixed location while moving the objective in precise steps. These images are used to calibrate the system for each bead independently.

Thereafter the objective is maintained very precisely in a fixed location, and the ring pattern can then be used to track the distance of the bead from the focal point along the optical z-axis, via cross reference to the calibration set.

This optical approach to bead position determination is effective. However, it suffers from a number of drawbacks that affect the cost and scalability of the approach.

Indeed, to perform an analysis of nucleic acid molecules, it is needed to achieve nearly single base resolution, which is in the range of 1 nanometer of bead movement, as 1 nanometer equals the distance increase each time one dsDNA base pair opens in an unzipping configuration. This distance is the sum of the extension of the ssDNA single nucleotide of the two complementary bases that have opened. The situation is analogous for a RNA molecule.

This level of resolution is achievable with the optical approach disclosed hereinabove. However, such a system requires a quite complex mechano-optical setup, and with a relatively small field of view, which limits the number of beads that the system can analyze simultaneously. For instance, a 30× objective can have a field of view of about 300 by 300 microns, which allows analyzing only about 1000 beads.

By contrast, it Is preferable for particular applications to perform analysis of many more molecules simultaneously; such as for instance up to $10^9$ molecules.

Moreover, even though the optical approach allows analyzing about 1000 beads simultaneously, it requires to generate a set of calibration images for each bead, which is time consuming and computationally intensive. Thus, making higher throughput with the same optical approach is quite complicated.

SUMMARY OF THE INVENTION

One aim of the invention is to overcome the aforementioned disadvantages of the prior art by providing a system and process for analyzing nucleic acids molecules, which allow the simultaneous analysis of a higher number of molecules than the prior art.

Another aim of the invention is to keep at least the same resolution than the prior art to perform precise analysis of the molecules.

To this end, a device for performing analysis of nucleic acid molecules is disclosed, comprising:
- a bead, on which one molecule can be anchored at one end,
- a surface, on which the molecule can be anchored at the other end,
- an actuator, adapted to cause the bead to move relative to said surface in one direction of motion,
- a sensor, adapted to measure a distance between the bead and the surface, the device being characterized in that it further comprises a well, having an axis extending along the direction of motion of the bead and a bottom which is formed by said surface, said well being filled with electrically conductive solution, and the bead being received in the well, and in that the sensor is adapted to measure an impedance of the well, said impedance depending on a distance between the bead and the surface, to determine, from the measured impedance, the distance between the bead and the surface.

In some embodiments, the device may comprise at least one of the following features:
the sensor may comprise:
- a main electrode, positioned on top of the well, in contact with the electrically conductive solution, the electrode being submitted to a known potential,
- a secondary electrode at the bottom of the well, carrying the surface to which the molecule can be anchored, and
- an electronic circuit, adapted to measure a current flowing between the electrodes.

The electronic circuit may comprise:
- a current to voltage amplifier connected to the secondary electrode,
- a voltmeter adapted to measure an output voltage of the current to voltage amplifier, and a computing circuit adapted to compute an impedance of the well from the measured voltage.

The area of a cross-section of the well transversal to its axis may be strictly increasing from the bottom of the well to the top.

The area of the cross-section at the bottom of the well may be greater than the area of the largest cross-section of the bead.

The well may have a shape of a truncated cone.

The area of the cross-section of the well may grow linearly with the distance from the bottom of the well.

The cross-section of the well may for instance be circular at its bottom and grow linearly in a direction orthogonal to the axis of the well with the distance from the bottom of the well.

The actuator may comprise at least one magnet mounted to be displaceable along the direction of the axis of the well, and the bead is made in a paramagnetic material, and is interposed between the bottom of the well and the magnet.

The device may comprise a plurality of identical beads and a plurality of identical wells, each adapted to receive one bead. Furthermore, in an embodiment in which the sensor comprises a main electrode, a secondary electrode, and an electronic circuit, adapted to measure a current flowing between the electrodes, said sensor may comprise a plurality of secondary electrodes, each disposed at the bottom of a respective well and forming a surface to which is anchored a respective bead, and the electronic circuit may then a plurality of current to voltage amplifiers, each connected to a respective secondary electrode, with the computing circuit further adapted to simultaneously measure output voltages of the current to voltage amplifiers and compute the impedances of the respective wells.

The device may comprise a plate of electrically insulating material in which the wells are formed, all wells opening out at a top surface thereof, and the actuator further comprising a plurality of bars made of magnetic material, each bar being disposed on the top surface and extending between two adjacent wells.

Each bar may have a length inferior to 10 μm, and each bead may have a diameter inferior or equal to 1 μm.

An analysis process of nucleic acid molecules is also disclosed, said process being implemented by a device according to the above description, and comprising at least one step of measuring a distance between the bead and the bottom of the well, each measuring step comprising measuring an impedance of the well in view of determining a position of the bead in the well.

In an embodiment, the analysis process may also comprise a preliminary step of anchoring at least one molecule to a bead and the bottom of a well, said step comprising:
positioning at least one bead on which a molecule is anchored in the solution filling the well,
applying a first potential difference between main and secondary electrodes of the sensor to drive the bead in contact with the bottom of the well, and
reversing the potential difference between the electrodes.

The device according to the invention allows analyzing a molecule attached at one end to a micro-bead and at the other to the bottom of a well. By monitoring the impedance changes of the well according to the position of the bead in the well one can measure its position with great precision.

Indeed, the overall conductance of the well corresponds to the conductance of the solution that fills the well. When the bead moves inside the well and occupies a portion of the latter, it reduces the cross-section of the well that is filled with the electrically conductive the solution and thus changes the conductance of the well.

Therefore, by determining an exact shape of the well, and in particular when the well has a cross-section area increasing with the distance to the bottom of the well, a position of the bead in the well can be easily determined.

This device can be multiplexed to allow simultaneous analysis of a great number of nucleic acid molecules, without reducing the resolution. Indeed, when the device comprises a plurality of wells and respective beads, all the beads can be monitored by a sensor comprising, for each well, a secondary electrode and a current to voltage amplifier allowing precise monitoring of the position of each bead in its respective well.

BRIEF DESCRIPTION OF THE DRAWINGS

The features and advantages of the invention will be apparent from the following more detailed description of certain embodiments of the invention and as illustrated in the accompanying drawings, in which:

FIG. 2 shows the resistance of the well according to the position of the bead, in the embodiment of FIG. 1a.

DETAILED DESCRIPTION OF A PREFERRED EMBODIMENT OF THE INVENTION

Device for the Analysis of Molecules
Overall Description of the Device

Figure 1A:
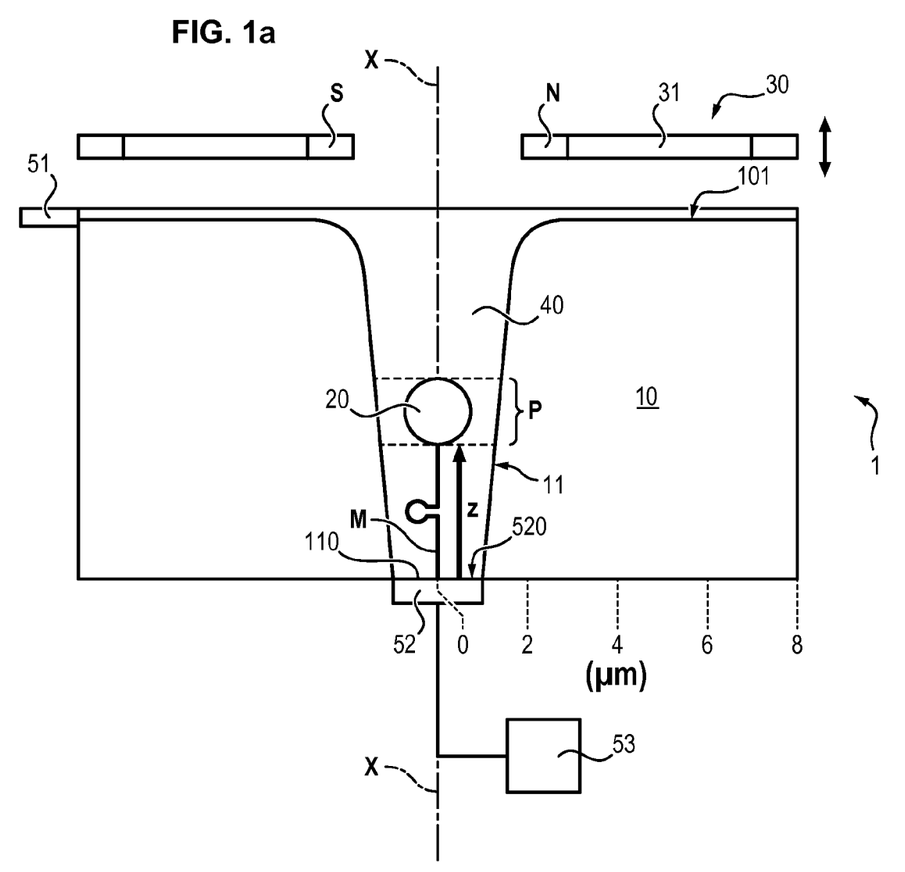
FIG. 1a shows an exemplary embodiment of a device for analysing nucleic acid molecules, FIGS. 1b and 1c respectively show a cross-sectional view and a perspective view of possible shapes of a well of a device.

With reference to FIG. 1a, a device 1 for analysing nucleic acids molecules is shown. These molecules may in particular be DNA or RNA molecules. Preferably, as shown in the figure, the molecule may be a double-stranded molecule of the hairpin type.

Hairpin means a double helix wherein the 5' end of one strand is physically linked to the 3' end of the other strand through an unpaired loop. This physical link can be either covalent or non-covalent, but is preferably a covalent bond.

Thus a hairpin consists of a double-stranded stem and an unpaired single-stranded loop.

The device 1 comprises a plate 10 of electrically insulating material. For instance the plate can be made of silicon, glass, a non-conducting polymer or resin.

At least one well 11 is made within the plate, each well extending along a main axis X-X which is orthogonal to the plane in which the plate extends. Each well opens out at a top surface 101 of the plate.

Moreover, each well 11 has a bottom 110, preferably extending orthogonally to said axis X-X.

The wells are so-called microwells, because the order of magnitude of their dimensions (depth, largest length of a cross-section) is about 1 μm or about 0.1 μm. For instance, a well can have a depth along the X-X axis of a few micrometers, for instance comprised between 1 and 10 micrometers, for instance equal to 8 μm.

A largest length of a cross-section of the well in a plane orthogonal to the X-X axis can range from a few hundreds nanometers to a few micrometers, for instance about 4 or 5 μm as shown in FIG. 1.

Existing techniques allow producing such wells, such as for instance a technique called track etching technique, comprising a step or irradiation with heavy ions to form latent tracks and a step of chemical etching. For more details about techniques for producing those wells, one may refer for instance to the works of the Siwy Research Lab (website of the lab: http:/www.physics.uci.edu/~zslwy/fab.html) or the publication by M. Davenport, K. Healy, M. Pevamlk, N. Teslich, S. Cabrini, A. P. Morrison, Z. S. Siwy and S. E. Létant, "The Role of Pore Geometry in Single Nanoparticle Detection", In ACSNANO, vol. 6, n°. 9, 8366-8380, 2012.

The device furthermore comprises at least one bead 20. Preferably, the device comprises a plurality of beads 20, in equal number to the number of wells.

The number of wells and beads may preferably be greater than 1000, for instance greater than 10000, for instance about 100000 or 1000000.

Each bead is spherical and has a diameter not greater than 5 μm. For instance, the bead 20 may have a diameter of about 1.5 μm or 1 μm. Preferably, the bead may be even smaller and have a diameter of less than 1 μm, for instance of 0.3 μm.

As non-limiting examples, the following references of beads can be used:
  MyOne, produced by Invitrogen, having a diameter of 1.04 μm
  M270, produced by Invitrogen, of 2.8 μm diameter,
  M450, produced by Invitrogen, of 5.5 μm diameter,
  Ademtech 500, produced by Ademtech, of 0.5 μm diameter,
  Ademtech 300, produced by Ademtech, of 0.3 μm diameter.

To perform an analysis of a nucleic acid molecule, one molecule M is anchored to the bead 20 at one end thereof, and to the surface of the bottom of the well 110 on its other end.

To achieve anchoring of the molecule on the bead and on the bottom surface of the well, the bead and the surface may be coated with a specific material adapted to bind with an end of the molecule.

For instance, the DNA or RNA molecules may be labelled with biotin at one end, digoxigenin at another end, and the beads may be coated with streptavidin to bind with a labelled (for example biotin) end of a DNA/RNA hairpin molecule, and the bottom of the well 110 may further be coated with anti-Dig antibodies to bind a Dig-labelled end of the DNA/RNA molecule, see for instance Hunter M M, Margolies M N, Ju A, Haber E, "High-affinity monoclonal antibodies to the cardiac glycoside, digoxin, Journal of Immunology, 1982 September; 129(3): 1165-1172.

Therefore the bead is attached to the bottom 110 of the well 11 via the molecule.

Moreover, the bead 20 is free to move relative to the bottom 110 of the well 11. In particular, the bead 20 can move along the direction of the X-X axis. In order to control the motion of the bead 20 along this axis, the device 1 further comprises an actuator 30 adapted to cause the bead 20 to move in translation along said axis.

According to a preferred embodiment, the control of the motion of the bead may rely on a magnetic force applied by the actuator 30 on the bead 20. In that case, the bead is made of a paramagnetic material, such as a superparamagnetic material. For instance, the bead may be made in latex with incorporated ferrites, and coated with streptavidin for anchoring the molecule M.

The actuator 30 may comprise at least one permanent magnet 31, which can be controlled to move in translation along the X-X axis. Preferably, as shown in FIG. 1, the actuator 30 can comprise two permanent magnets 31, positioned at equal distance of the X-X axis and having their magnetic poles aligned perpendicular to the X-X axis, the North pole of a magnet facing the South pole of the other.

The bead 20 is positioned between the bottom 110 of a well 11 and the magnets 31.

These magnets allow one to apply a force on the bead and consequently on the molecule to which it is anchored. By moving the magnets closer to or further from the bead 20 in the direction of the X-X axis, one changes the magnetic field and thus controls the magnitude of the force applied to the bead, thus controlling the stretching of the sample in the direction of the X-X axis.

Another embodiment of the actuator 30 may comprise a permanent magnet and a strip covered with a magnetisable material positioned at a fixed distance relative to the well 11, of about a few micrometers. By bringing the permanent magnet closer or further from the strip covered with magnetisable material the field applied by said strip on the bead can be varied (see also embodiment disclosed in the section Disposition with a plurality of wells below).

Other ways of controlling the motion of the bead 20 can be used, such as optical or acoustic tweezers, the latter implying application of acoustic waves on the bead, see for instance G. Sitters, D. Kamsma, G. Thalhammer, M. Ritsch-Marte, E. J. G. Peterman and G. L. J. Wuite, "Acoustic Force spectroscopy", in Nature Methods, Vol. 12, N° 1, January 2015, or X. Ding, Z. S. Lin, B. Kiraly, H. Yue, S. Li, I. Chiang, J. Shi, S. J. Benkovic and T. J. Huang, "On-Chip Manipulation of single microparticles, cells, and organisms using surface acoustic waves", PNAS, Jul. 10, 2012, vol. 109, n°. 28, 11105-11109.

Change in Well Impedance with the Position of the Bead

Last, the device 1 allows determining the distance between the bead 20 and the bottom 110 of the respective well 11, corresponding to the length of the molecule anchored to the bead and the bottom 110 of the well, by monitoring the impedance, in particular the resistance (or conductance) of the well.

To this end, each well 10 is filled by an electrically conductive solution 40.

The electrically conductive solution 40 preferably has a conductivity of between $10^{-7}$ S/cm and $10^1$, preferably between $10^{-3}$ and $10^{-2}$ S/cm.

For instance, the solution 40 may be an aqueous solution of sodium chloride at a concentration of 100 mmol/m$^3$ (100 mM). The solution 40 may alternatively comprise a buffer compatible with the preservation of DNA molecules, such a buffered aqueous solution containing 10 mM Tris HCl and 0.1 mM EDTA and sodium Chloride at 100 mM. The buffer may also contain divalent cations compatible with enzymatic activities, such a 10 mM $MgCl_2$. In some embodiments, the buffer should support electrophoresis (e.g. Tris Borate EDTA buffer).

As can be seen in FIG. 1a, the electrically conductive solution 40 completely fills each well 11 and covers the top surface 101 of the plate.

The bead 20 must have a different conductivity than the conductivity of the solution. The bead preferentially is electrically insulating.

Moreover, the well 11 has a cross-section that varies with z, z being the distance along the X-X axis from the bottom of the well. This distance can be measured from the closest point of the bead to the bottom of the well, or from the centre of the bead.

Figure 1B:
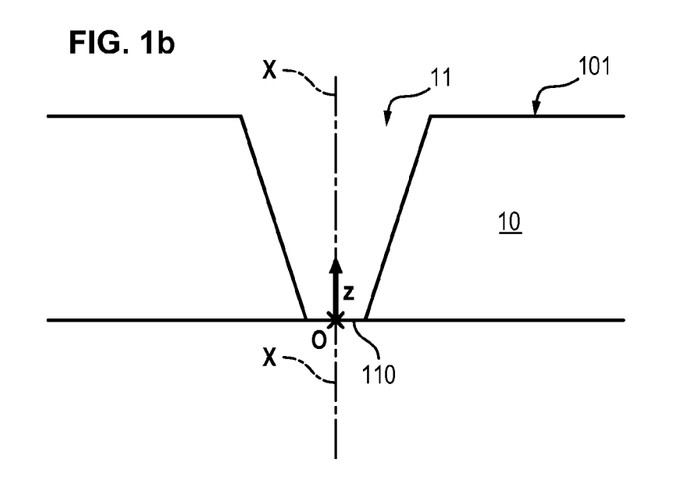
Figure 1C:
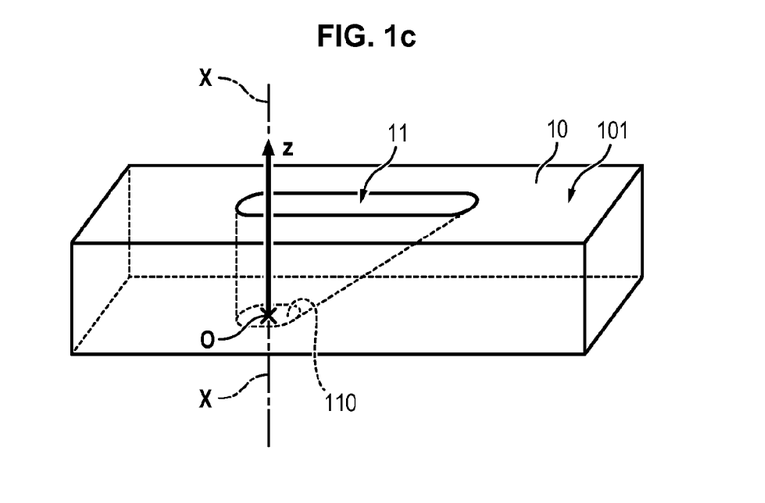

Preferably, the area of a cross-section of the well 11 transversal to the X-X axis strictly increases with the distance z from the bottom of the well (the z axis is shown on FIGS. 1*a* to 1*c* with the origin of the axis at the centre of the bottom of the well).

Therefore, as the bead 20 is of constant size, it occupies a varying proportion of the internal volume of the well.

For instance, if the bead is very close to the bottom of the well, it occupies a major proportion of the portion P of the well extending around the bead. The portion P is defined as the volume of the well extending between the cross-sections occupied by the lowest and highest points of the bead. The resistance of this portion is therefore increased dramatically because there is very little space left for the conductive solution. As the overall resistance of the well is the integral of the resistance along the whole depth of the well (along the X-X axis), the overall resistance is also increased dramatically.

On the contrary, if the bead is close to the top surface of the plate, it occupies a minor proportion of the portion P of the well extending around the bead. The resistance of this portion is thus less increased than in the previous example, and the overall resistance of the well is smaller than that of the previous example.

Figure 2:
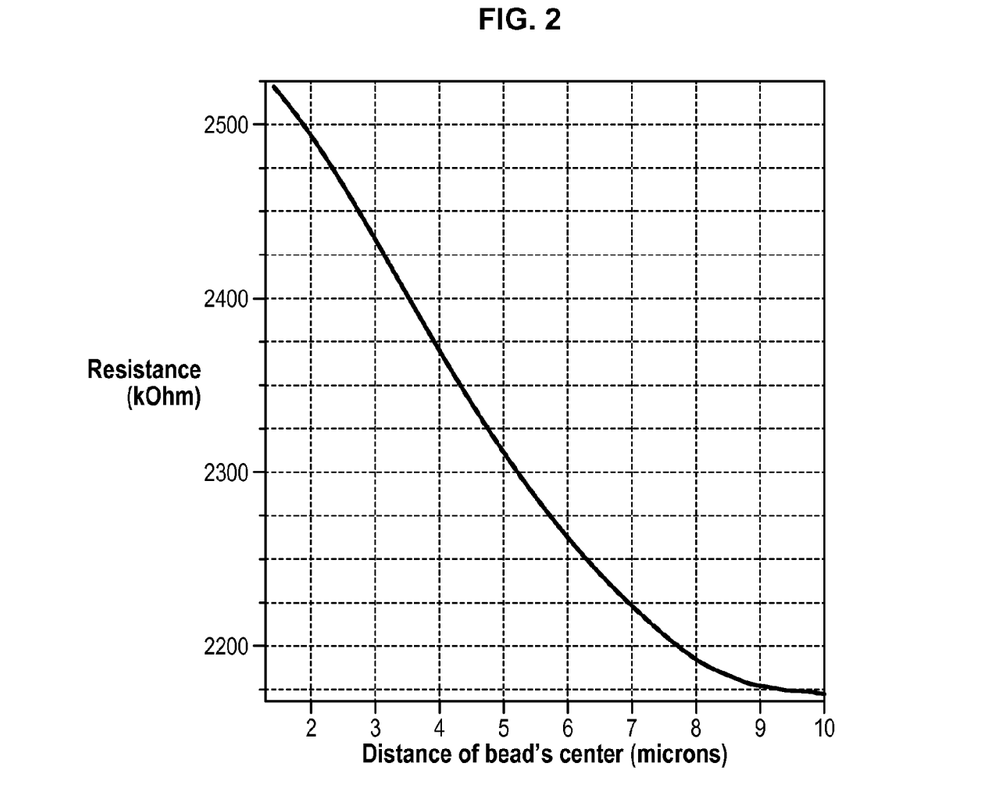

Therefore as shown for instance in FIG. 2, a curve showing the resistance of the well as a function of the distance of the bead from the well's bottom can be generated, in which each resistance value corresponds to a single distance value between the bead and the bottom of the well. By measuring the resistance value of the well it is therefore possible to infer with good precision the corresponding distance of the bead from the bottom of the well.

In order to obtain a good precision in determining the position of the bead 20 within the well 11, the smallest cross-section of the well is preferably larger than the largest cross-section of the bead. In particular, in the preferred case where the area of the cross-section of the well transversal to its axis is strictly increasing with the distance from the bottom, the smallest cross-section is located at the bottom 110 of the well. The fact that this cross-section is larger than the bead allows the bead to reach the bottom of the well, and hence allows measuring all positions of the bead in the well, including a position in which the distance between the bead and the well is null.

The well can have various different shapes. First, the well may be rotationally symmetric around the X-X axis.

For instance, as shown on FIG. 1*b*, the well may have the shape of a truncated cone, the smallest section of which corresponds to its bottom 110.

Alternatively, on FIG. 1*a*, the radius r of the wall of the well is defined according to the distance z from the bottom by the following equation:

$$z = I_0 \tan h2(r - r_0)$$

Where $I_0$ is the height of the well and $r_0$ is the bottom radius of the well. This well shape gives the resistance curve of FIG. 2.

According to still a different embodiment, the well preferably has a cross section which area increases linearly with the distance from the bottom of the well. Therefore, the difference between the area of the cross-section of the well and that of the bead is proportional to the distance of the bead to the bottom of the well.

Thus, the resistance of the well decreases linearly with the increase of the distance between the bead and the bottom of the well.

For instance, as shown in FIG. 1*c*, the well may have an oblong cross section, formed, at the bottom 110 of the well, by a circular cross-section, which increases linearly with z along a direction orthogonal to the X-X axis of the well.

It is thus even easier to infer the position of the bead from a measure of the resistance of the well. In particular, the curve shown in FIG. 2 showing the resistance of the well according to the position of the bead for a well which geometry is shown in FIG. 1*a* becomes a straight line.

Impedance Sensor

Figure 3:
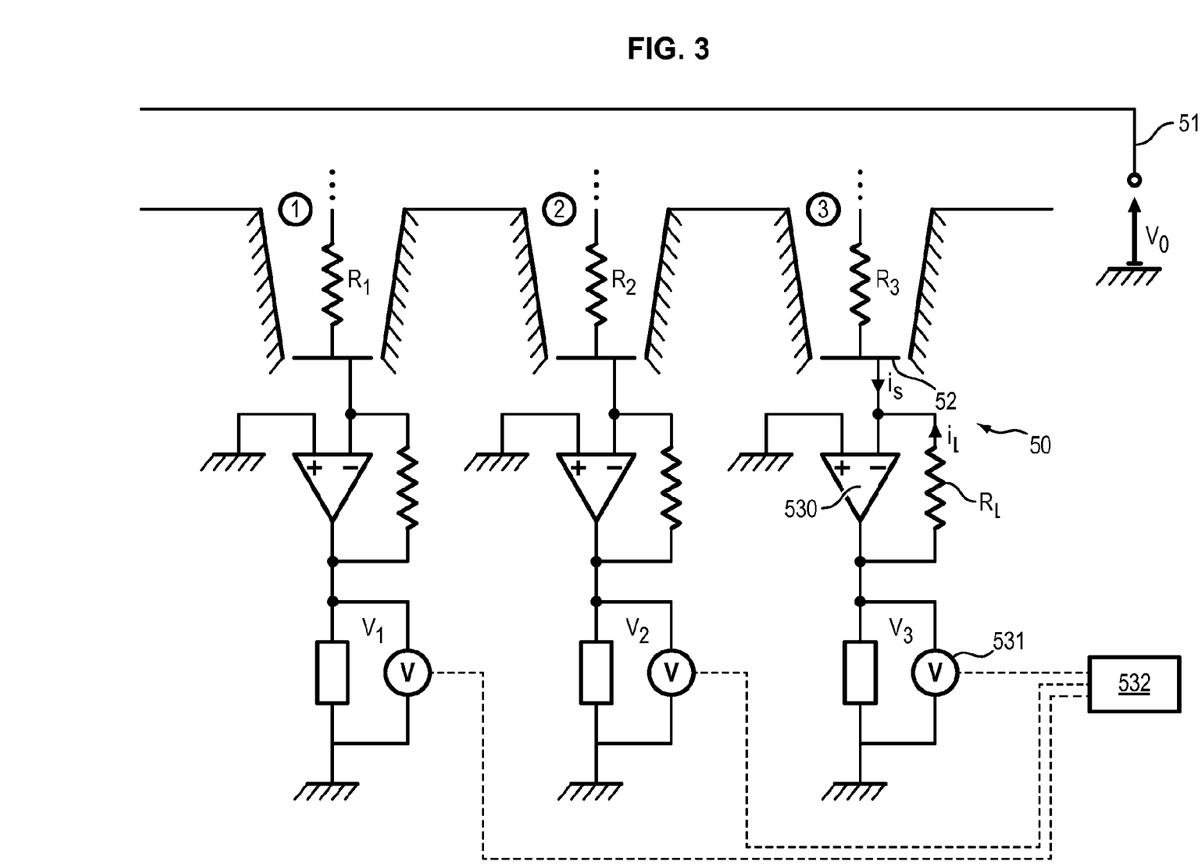
FIG. 3 schematically shows the electric equivalent circuit of a device according to an embodiment of the invention.

With reference to FIG. 3, the device 1 further comprises a sensor 50 which is adapted to measure an impedance of the well 11 and infer, from this measurement, a distance z between the bead 20 and the bottom surface 110 of the well 11.

The sensor 50 comprises a main electrode 51, which is able to set the electrically conductive solution 40 to a reference voltage $V_0$. As shown in FIG. 1*a*, the main electrode 51 is in contact with the electrically conductive solution 40. Preferably, the main electrode 51 can lie on the top surface of the plate 10. As the conductive solution extends over said top surface, it is in contact with the main electrode 51. The main electrode 51 is of course connected to a voltage source (not shown), preferably a DC voltage source.

The voltage $V_0$ preferably is a constant voltage. It is preferably below 0.5 V to avoid electrolysis phenomenon inside the well. Preferably, the voltage $V_0$ is comprised between 10 and 500 mV, even preferably comprised between 50 and 300 mV. For instance, the voltage $V_0$ may be equal to 0.25V.

Moreover, the sensor 50 comprises at least one secondary electrode 52. More specifically, the sensor 50 comprises secondary electrodes 52 in equal number to the number of wells 11, being also the number of beads 20. Each secondary electrode 52 may be a gold or platinum electrode.

The secondary electrode 52 forms the bottom 110 of the well and has a surface 520 forming the surface to which the molecule is anchored.

On FIG. 3, the columns of conductive solution 40 with variable positions of the respective beads form resistances which are equivalent to resistors R1, R2, R3. Each resistor has one pole in contact with the main electrode 51, and the other pole in contact with the secondary electrode 52 at the bottom of the well.

The sensor 50 further comprises an electronic circuit 53 which measures the resistance of the well by measuring the current flowing through the well. To this end, according to one embodiment, the electronic may comprise a determined resistance connected in series with the secondary impedance. A potential difference at the poles of the resistance may be measured to infer the current flowing through the resistance.

However this embodiment may not be precise because the currents flowing in each well are very low. The electronic circuit 53 therefore preferably comprises an amplification of the current flowing in the wells.

To this end, the electronic circuit 53 preferably comprises one current to voltage amplifier 530 for each secondary electrode.

This current to voltage amplifier comprises an operational amplifier which inverting input is connected to the secondary electrode 52, non-inverting input is connected to the ground, and output is connected to the inverting input through a feedback resistance of known value.

The current $i_1$ flowing between the main electrode 51 and one secondary electrode 52 is given by the following equation:

$$i_i = \frac{V_- - V_0}{R_i}$$

Where $V_-$ is the potential of the inverting input of the operational amplifier, and $R_i$ the resistance value of the $i^{th}$ well.

As the two inputs are theoretically at the same potential: $V_-=0V$ and hence:

$$i_i = \frac{-V_0}{R_i}$$

Moreover, in the feedback loop, the current k can be expressed by the following equation:

$$i_l = \frac{V_- - V_i}{R_l} = \frac{-V_i}{R_l}$$

Where $R_l$ is the value of the resistance of the feedback loop and $V_i$ the output potential of the current to voltage amplifier 530.

Hence, by measuring the potential $V_i$, one can obtain the value of the current ii flowing inside the $i_{th}$ well by this equation:

$$i_i = -i_l = \frac{V_i}{R_l}$$

Moreover, one can then obtain the value of the resistance of the well:

$$R_i = -\frac{V_0}{V_i} R_l$$

The electronic circuit 53 therefore further comprises a device 531 adapted to measure the potential $V_i$, for instance a voltmeter, as well as a computing circuit 532, comprising for instance a processor, controlling the acquisition measurements by the device 531, and inferring the value of the resistance from the measured potential. The processor is preferably adapted to run a dedicated program comprising a set of instructions for controlling the sensor (in particular the measurement device 531), inferring the value of the resistance of each well as well as the corresponding distance of each bead from the bottom of the respective well.

Preferably, the measurements are achieved over the whole device at a measuring sampling rate of about 50 Hz (measurement performed in parallel at the sampling rate over all the wells of the device). The measured potential should be integrated or averaged between two measurements to reduce noise or suppress parasite signal. In that respect the sampling rate may be a multiple of the main power frequency.

Detailed Implementation Example

An implementation example is detailed with reference to the attached drawings. FIG. 1a illustrates the case of a single microwell 11 whose profile is described by the equation:

$$z = I_0 \tan h2(r-r_0)$$

With $I_0=8$ μm being the height of the well and $r_0=2$ μm being the bottom radius of the well. The well is partially obstructed by a bead of diameter d=1.5 μm.

This well is filled with an aqueous solution of sodium chloride at a concentration of 100 mol/m3, corresponding to a conductivity o=$10^{-2}$ S/cm.

For a voltage across the well V, the current in the well is I=V/R, with R the equivalent resistance of the well filled with solution 40 and partially obstructed by the bead. Said resistance is shown in FIG. 2 as a function of the distance of the bead's centre from the bottom of the well. One can see that by measuring the resistance of the well, the position of the bead can be inferred by reporting the resistance value on this curve and determining the corresponding distance.

The electronic current noise measured over a bandwidth Δf can be due to two sources:

Johnson noise, also called thermal noise, being the electronic noise generated by the thermal agitation of the electrons, this noise being expressed by the following equation:

$$inJ = \sqrt{4k_B T \Delta f R}$$

Where T is the ambient temperature, kB is the Boltzmann constant, and

Shot-noise (associated with the stochastic flow of elementary electron charges, which is expressed by the following equation:

$$inS = \sqrt{2Ie\Delta f}$$

Where I is the signal current in the well and e the elementary charge carded by an electron (in absolute value).

One can see that, for a voltage V superior to $2k_bT/e$, that is about 50 mV at ambient temperature of about 293K, the Johnson noise is dominated by the shot noise associated to the signal current. Moreover, said shot noise increases with the resistance of the well. Thus in order to keep the signal to noise as high as possible the size of the well may not be too small; for instance a well having dimensions of the order of magnitude of 1 nm ("nanowell") would provide results too noisy to be exploited.

Back to this example, the voltage applied by the main electrode 51 equals 0.25V. According to FIG. 2, the maximal resistance of the well for the electrolyte solution of this example is about 2500 kΩ. For such a voltage the current is I=V/R=100 nA and the current noise is inS≈2 pA (for a bandwidth Δf=100 Hz).

The change of impedance ΔR over a distance δI=5 μm is about 300 kΩ, which means that to resolve a change of distance of about 1 nm (which corresponds to a single base-pair in a double stranded DNA molecule of 2500 base pairs), one has to be able to resolve a change in impedance of δR=0.06 kΩ. This corresponds to a change in current δI=I. δR/R=2.5 pA, which corresponds to a signal/noise ratio of about 1.

Averaging over Δf=1 Hz allows yielding single base pair detection with a comfortable signal/noise ratio of 10.

Disposition with a Plurality of Wells

As indicated above, the device 1 disclosed hereinabove preferably comprises a plurality of wells 11 and an equal number of beads 20, the wells being packed at high density on a chip, for instance at a density comprised between $10^5$ and $10^8$ wells/cm$^2$, for instance if each microwell device has a largest cross-section (at the top surface of the plate) of 5×5 microns, about $4 \cdot 10^6$ Wells per square centimeter should be obtained.

In that case the sensor 50 is easily multiplexed by providing an equal number of secondary electrodes 52, and current to voltage amplifiers 530, in order to allow parallel measurement of the conductivity of the wells, in a similar manner to a CMOS camera comprising a plurality of pixels, and measuring the photo-current of each pixel.

The computing unit 532 is however common to all the wells 11.

To keep the computational requirements of the computing unit 532 as low as possible, all the beads and all the wells are preferably identical, with the tolerance given by the manufacturing processes. Furthermore, a single main electrode 51 is common to all the wells 11 and applies the same voltage $V_0$ to all the wells, since it is in contact with the electrically conductive solution 40 which fills all the wells and extends over the top surface 101 of the plate 10.

Furthermore, in the case of many wells 11 arranged in a common plate 10, the actuator 30 may preferably comprise a pair of main macroscopic permanent magnets 31, which is displaceable in translation along the X-X axis, and covers substantially all the surface of the plate 10 in order to generate a homogenous magnetic field.

The actuator 30 further comprises a plurality of bars 32 made of magnetic material, such as for instance an alloy of iron and nickel known under the trade name of Permalloy®, that are fixed on the plate 10.

Figure 4A:
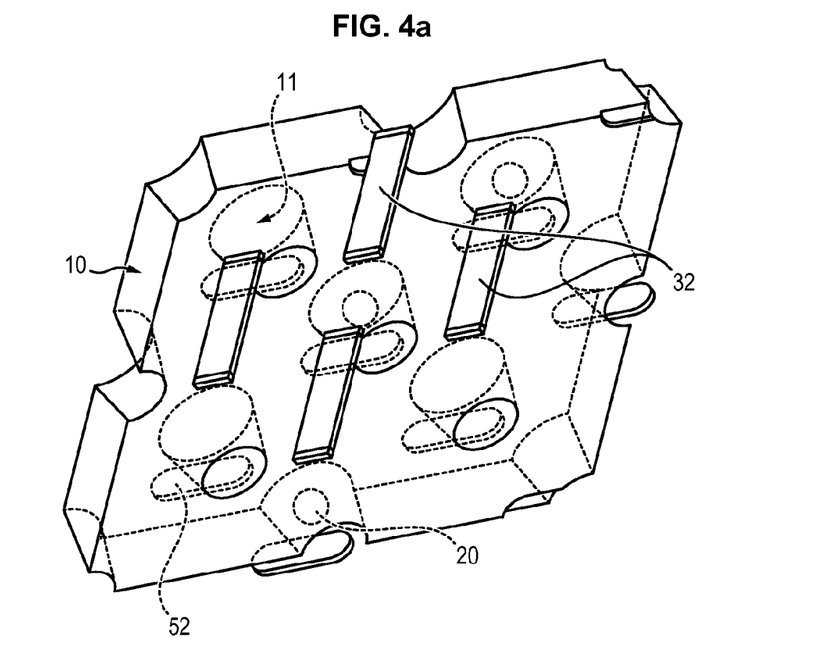
FIGS. 4a and 4b are schematic drawings of an analysis device according to two embodiments.
Figure 4B:
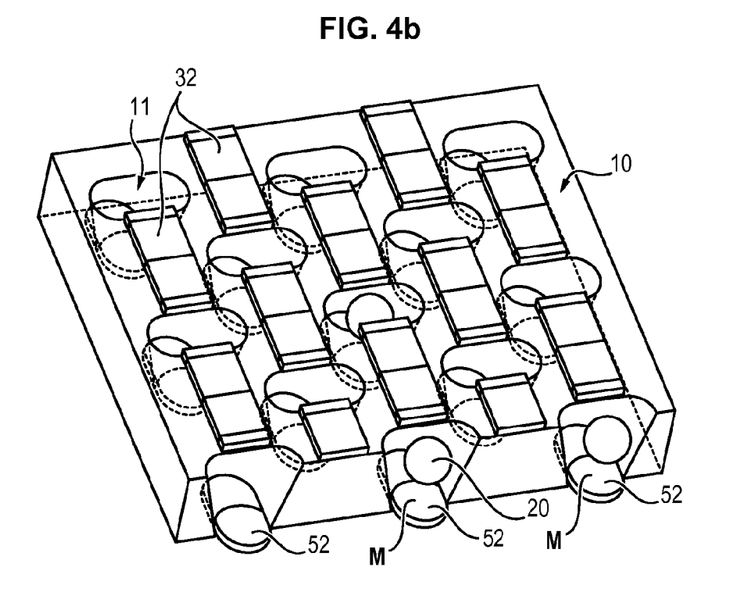

As shown on FIGS. 4a and 4b, each bar 32 is positioned on the plate 10, on the top surface 101 thereof. Each bar 32 extends between two adjacent wells in order for a polar end 320 of a bar 32 to be flush with an edge of the well. Therefore the bars 32 are very close to the beads 20. One understands that when wells are packed at high-density in a plate 10, the distance between two adjacent wells is of the order of magnitudes of some μm or some tens of μm. Therefore the magnetic bars 32 have lengths of the same order of magnitude.

Figure 5A:
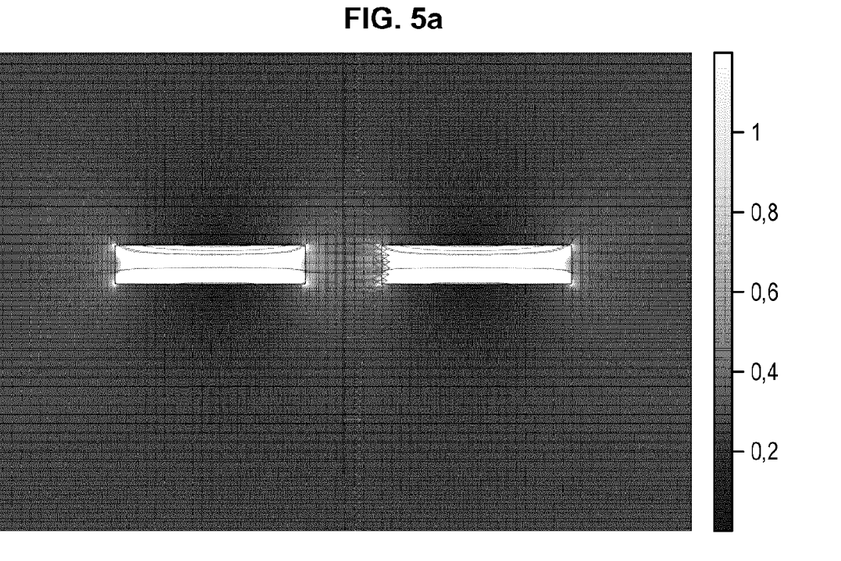
FIGS. 5a and 5b show the gradient of magnetic field exerted on a bead in an exemplary analysis device.

According to the example shown in FIG. 5a, the magnetic bars 32 for instance have a length of 8 μm, a width of 1 μm and are spaced apart by a distance of 2 μm.

Each bar 32 of magnetic material is magnetized under the influence of the magnetic field produced by the main magnets 31. Therefore the displacement of the main magnets 31 to bring them closer or further from the plate 10 increases or reduces the magnetic field density between the bars, which in turn increases or reduces the force exerted on the beads.

This embodiment is particularly preferred because the magnetized bars 32 are smaller than the main magnets 31 and are closer to the beads 20. By diminishing the size of the magnets, the gradient of magnetic field in the vicinity of the beads 20 increases, and hence the magnetic force applied on the bead increases.

Figure 5B:
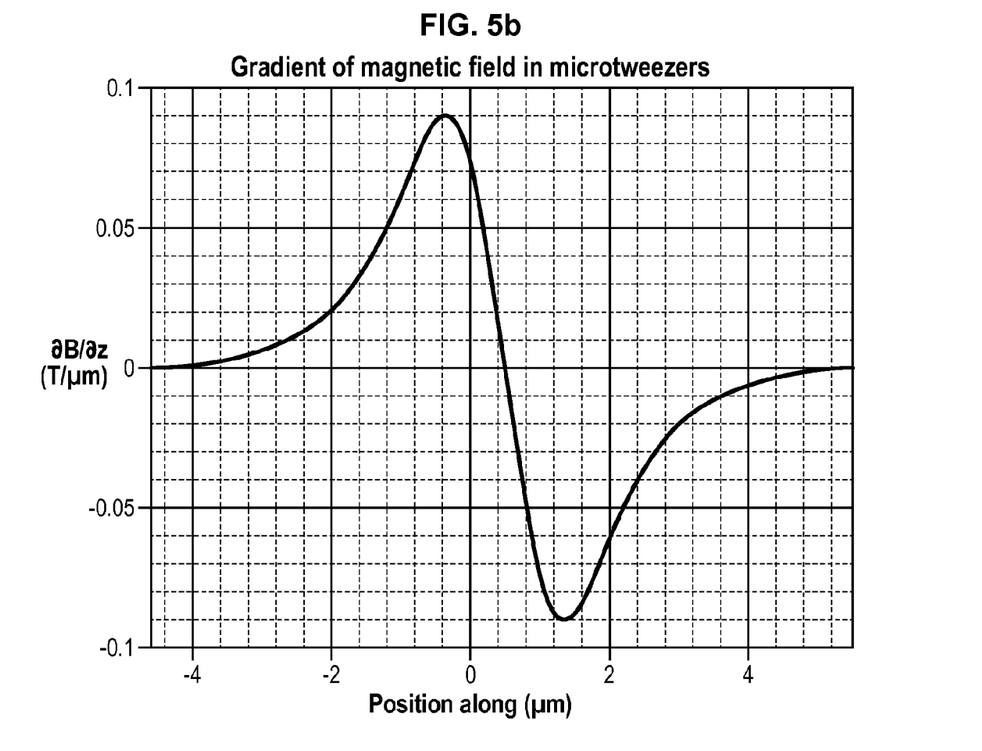

Indeed, simulations reproduced in FIGS. 5a and 5b have shown that, when the bars 32 of magnetic material are exposed to a homogeneous magnetic field of 0.088 T generated by the main magnets 31, the field is enhanced between the bars 32, which produce a significant field gradient along the X-X axis. As visible in FIG. 5b, the maximum value of this field gradient is about 0.09 T/μm, that is to say $90 \cdot 10^3$ T/m.

The magnetic force applied of the beads depends on this field gradient. In particular, the maximum magnetic force (in N) applicable on a bead can be expressed as follows:

$$F_M = m_S \cdot \frac{dB}{dz}$$

Where m, is the saturation value of the magnetic moment of the bead, in A·m$^2$ and dB/dz is the gradient of the magnetic field, in T/m.

Here are the saturation values of the magnetic moments of the beads according to the examples given above:
MyOne by Invitrogen: $13.2 \cdot 10^{-15}$ A·m$^2$
M270 by Invitrogen: $57.5 \cdot 10^{-15}$ A·m$^2$
M450 by Invitrogen: $238.5 \cdot 10^{-15}$ A·m$^2$
Ademtech 500: $4.7 \cdot 10^{-15}$ A·m$^2$
Ademtech 300: $1.017 \cdot 10^{-15}$ A·m$^2$ Therefore the magnetic force applied on the bead can for instance exceed 1000 pN for a MyOne type bead with the configuration shown in FIG. 5.

By contrast, without the magnetized bars 32 interposed between the plate 10 and the main magnets 31, the maximum field gradient resulting from the magnets is about $1.66 \cdot 10^3$ T/m. This maximum field gradient gives a maximum force exerted on a bead of about 22 pN for a MyOne type bead. Thus the presence of the magnetized bars allows obtaining a magnetic force on the beads which is about 55 times greater than without the magnetized bars 32.

This increase of magnetic force applied to the beads 20 makes it possible to reduce the size of the beads, while maintaining a force at least equivalent, or even greater to, that which was applied on the beads by the magnets shown in FIG. 1a.

The reduction of the size of the beads in turn allows reducing the size of the wells, and hence increasing the density of the wells and the device throughput. Therefore, the number of molecules which can be simultaneously analysed can reach $5 \times 10^7$ molecules/cm$^2$ (assuming a bead diameter of 300 nanometers).

As shown in FIGS. 4a and 4b, wells can be packed in the plate 10 according to various configurations to reach various densities. For instance in FIG. 4a, a lower density of wells is shown than in FIG. 4b. In the latter, the wells 11 extends in one dimension orthogonal to the X-X axis, which allows a more linear conductivity with the position of the bead and also allows reducing the overall unit size, since the cross-section of a well only grows in one direction.

Process for Analyzing Nucleic Acid Molecules

Figure 6:
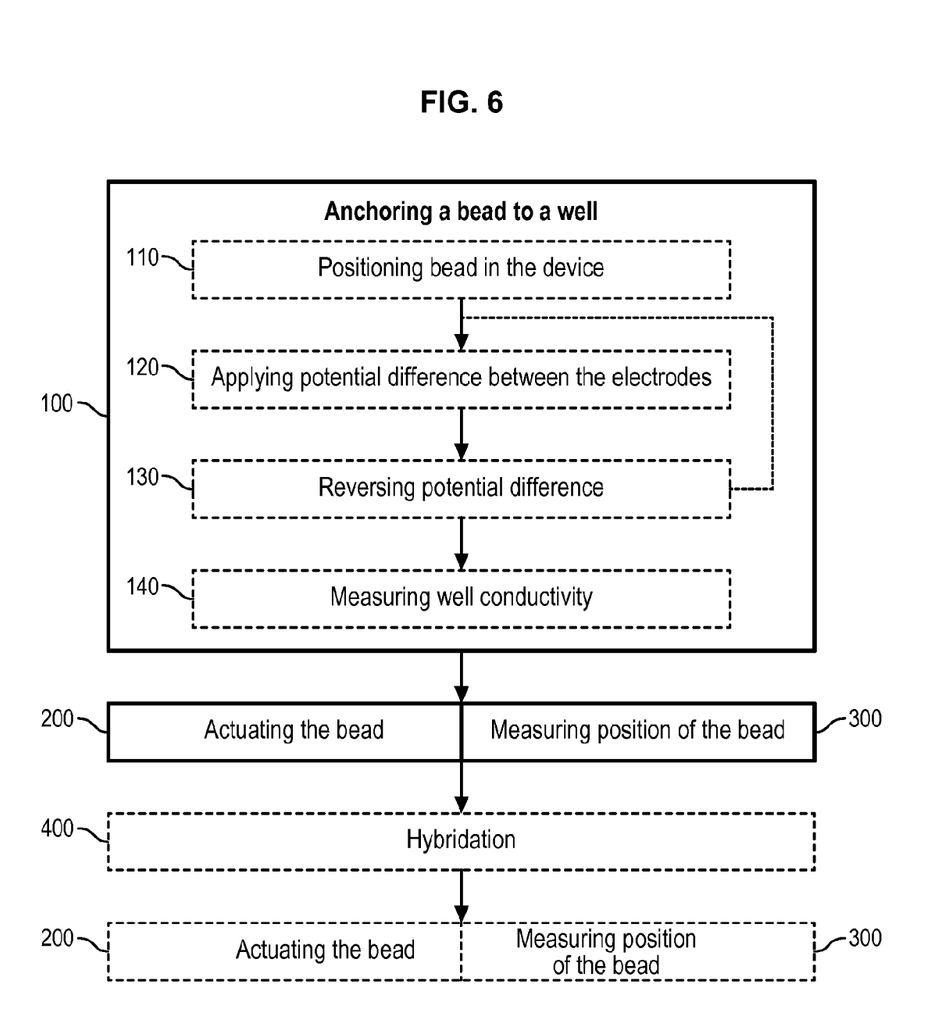
FIG. 6 shows the main step of an analysis process according to one embodiment of the invention.

With reference to FIG. 6, the main steps of a process for analysing nucleic acid molecules such as DNA or RNA molecules are shown. The analysis for example comprises the determination of a nucleic acid sequence, i.e. the deciphering of the actual succession of bases in a nucleic acid, but also the determination of other pieces of information on the nucleic acid sequence, such as the detection of a particular sequence in a nucleic acid molecule, the detection of a difference between the sequences of two different nucleic acid molecules, or the binding of a protein to a specific sequence, see e.g. WO 2011/147931; WO 2011/147929; WO 2013/093005; WO 2014/114687.

As previously indicated, the analysed molecules M are of hairpin type. In a hairpin molecule, the ends of the two strands which are not engaged in the loop are attached respectively to the bead and the bottom of the well and can thus be pulled apart upon motion of the bead. It is even possible to completely open a hairpin double-stranded nucleic acid molecule by pulling on each end of the molecule which a determined force.

The process will be described for a single bead in a single well but is applicable to any number of wells.

This process comprises a first step 100 of anchoring a bead to the bottom of a well via a nucleic acid molecule M, that is to say obtaining a first end of the molecule M anchored to a bead 20 and the second end of the molecule anchored to the bottom of a well 11.

The above-disclosed structure of the device allows performing this step according to a preferred embodiment, especially when the device comprises a large number of wells packed at high density in a plate. According to this embodiment, the step 100 comprises a first sub-step 110 of positioning the beads, with nucleic acid molecules attached thereto, are placed in the device, in the solution 40 above the wells 11.

A second sub-step 120 then comprises applying a potential difference between the main electrode 51 and the secondary electrodes to drive the beads towards the electrode 52 at the bottom of the well by electrophoresis. The potential difference applied between the electrodes is about a few V/cm. For more information about electrophoretic mobility of beads, see B. Xiong, A. Pallandre, I. le Potier, P. Audebert, E. Fattal, N. Tsapis, G. Barratt and M. Taverna, "Electrophoretic mobility measurement by laser Doppler velocimetry and capillary electrophoresis of micrometric fluorescent polystyrene beads", in Analytical. Methods, 2012, 4, 183.

Upon contacting the bottom of the well, at least one bead binds with the latter. Preferably, each well is designed such as to allow only one bead to bind with its bottom, i.e. the cross-section of the bottom of the well is smaller than twice the cross-section of a bead.

Then the anchoring step 100 comprises a third sub-step 130 of reversing the voltage between the electrodes. Thereby, all the unbound beads are driven out of the well.

These sub-steps 120 and 130 can be performed repeatedly in order to maximize the overall loading efficiency of the wells.

Last, a sub-step 140 of measuring the conductivity of at least one well can be implemented to determine the presence or absence of a bounded bead in the well.

The process then comprises at least one step 200 of actuating the bead 20 by the actuator 30 to change a distance between the bead 20 and the bottom 110 of the well 11, thereby applying a tension on both ends of the molecules, and at least one step 300 of measuring a distance between the bead and the bottom of the well. This distance is measured by measuring the resistance of the well 11. As already detailed with reference to FIG. 3, this measurement is itself carried out by measuring the output voltage of the current to voltage amplifier 530.

The process may be implemented in many different manners, but it preferably comprises a sequence of a plurality of steps 200 of actuating the bead at different distances from the bottom of the well.

As shown on FIG. 6, the step 300 of measuring the distance between the bead 20 and the bottom 110 of the well 11 is in that case preferably implemented continuously during all the sequence of actuating steps 200.

Alternatively, the measurement step 300 may be carried out simultaneously with each actuating step.

As a non-limiting example, the process can for instance be carded out according to the sequence disclosed in document EP2390351, to which one can refer for more details about the implementation of the sequence. This sequence comprises:

a first couple of steps 200 and 300, during which the bead is actuated to separate the two strands of the hairpin molecule M, by applying a tension about 15 pN or more on the molecule, for instance equal to 18 pN. The distance between the bead and the bottom 110 of the well 11 is measured, which corresponds to the total length of the opened hairpin molecule.

a step 400 of hybridizing a piece of single-stranded nucleic acid molecule with one of the strands of the molecule M, a second couple of steps 200 and 300 a step of actuating 200 the bead to release the tension applied to the molecule. The nucleic acid molecule M then rezips to reform a hairpin.

However, the presence of a single-stranded nucleic acid molecule hybridized to one of the nucleic acid strands at step 400 leads to a pause in re-hybridization (or rezipping) of the hairpin. The detection of such a pause indicates that the single-stranded nucleic acid molecule comprises a sequence which is complementary to a part of the hairpin molecule M. Moreover the continuing measurement of the length of the molecule during the re-hybridization of the hairpin, including the measurement of the length of the molecule during the pause when the hairpin molecule is partly re-hybridized, allows determining the position of the said sequence in the molecule. Indeed, the comparison between the length of the molecule at the pause and the total length of the molecule allows inferring the exact position of the hybridized nucleic acid molecule, from which the sequence of the molecule M at said position can be deduced.

According to another non-limiting embodiment, the process may be carried out according to a sequence disclosed in document EP 2 390 350, to which one can refer for more implementation details.

The above-disclosed device and process show key improvements with regards to the optical detection system known in the prior art.

First, the position of each bead is deduced directly from changes in impedance of a simple well structure. This avoids the need for complex optical components.

Second, as previously explained, the beads as well as the wells, can be reduced in size. It is therefore possible to pack the wells at high density on a single chip and then read the impedances of the wells in parallel.

The above apparatus also have reduced computational requirements, because the relationship between the current in a well and the position of the bead needs little computation to calculate.

Last, as shown with reference to FIGS. 4a and 4b, it Is now possible to directly incorporate onto the plate the magnetic material allowing actuation of the beads. This results in much greater forces exerted on the beads and therefore possible diminution of the size of the beads and wells.

The invention claimed is:

1. Device for analyzing nucleic acid molecules, comprising:
    a well, comprising:
        (i) a bottom surface and a top surface opposite the bottom surface,
        (ii) an axis extending between the bottom surface and the top surface,
        (iii) a nucleic acid molecule anchored at a first end to the bottom surface;
        (iv) an electrically conductive solution, filling at least part of the well; wherein a cross-sectional area of the well perpendicular to the axis increases from the bottom surface to the top surface of the well; and a bead disposed within the well, the bead anchored at a second end of the nucleic acid molecule, the second end opposite the first end;

an actuator configured to cause the bead to move relative to the bottom surface along the axis of the well; and a sensor configured to measure an impedance of the well, the impedance depending on a distance between the bead and the surface, such that, from the measured impedance, the distance between the bead and the surface is determined.

2. The device according to claim 1, wherein the sensor comprises:

a main electrode, positioned on the top surface of the well, in contact with the electrically conductive solution, the electrode being submitted to a known potential, a secondary electrode adjacent the bottom surface of the well, , and an electronic circuit, configured to measure a current flowing between the electrodes.

3. The device according to claim 2, wherein the electronic circuit comprises:

a current to voltage amplifier connected to the secondary electrode, a voltmeter adapted to measure an output voltage of the current to voltage amplifier, and a computing circuit adapted to compute an impedance of the well from the measured voltage.

4. The device according to claim 1, wherein the area of the cross-section at the bottom of the well is greater than the area of the largest cross-section of the bead.

5. The device according to claim 1, wherein the well has a shape of a truncated cone.

6. The device according to claim 1, wherein the cross-sectional area of the well increases in a linear relationship with respect to the distance from the bottom surface of the well.

7. The device according to claim 6, wherein the cross-section of the well is circular at the bottom surface and increases linearly in a direction orthogonal to the axis of the well with the distance from the bottom surface of the well.

8. The device according to claim 1, wherein the actuator comprises at least one magnet mounted to be displaceable along the direction of the axis of the well, and the bead is made of a paramagnetic material, and the bead is interposed between the bottom surface of the well and the at least one magnet.

9. The device according to claim 1, further comprising a plurality of identical beads and a plurality of identical wells, each of the plurality of identical wells adapted to receive one bead.

10. The device according to claim 1, further comprising:

a plurality of identical beads and a plurality of identical wells, each of the plurality of identical wells having one bead of the plurality of identical beds therein, each well of the plurality of identical wells provided with a sensor, the sensor comprising:

a main electrode, positioned on the top of the well and in contact with the electrically conductive solution, the electrode being submitted to a known potential, a secondary electrode adjacent the bottom surface of the well, and an electronic circuit, configured to measure a current flowing between the electrodes, the electronic circuit comprises a current to voltage amplifier, the current to voltage amplifier connected to the secondary electrode, and a computing circuit configured to simultaneously measure output voltages of the current to voltage amplifier and compute the impedance of the respective wells.

11. The device according to claim 1, further comprising a plurality of identical beads and a plurality of identical wells, in which one bead of the plurality of identical beads is disposed, each of the identical wells adapted to receive one bead.

12. The device according to claim 11, wherein:

the actuator comprises at least one magnet displaceably mounted such that the at least one magnet is displaceable along the axis of the well; and the bead comprises a paramagnetic material and is interposed between the bottom surface of the well and the magnet.

13. The device according to claim 12, wherein the at least one magnet comprises a plurality of bars, the plurality of bars made of a magnetic material, and each bar of the plurality is disposed on a top surface of the plate between two adjacent wells of the plurality of wells.

14. The device according to claim 13, wherein each bar of the plurality of bars has a length less than 10 μm and has a diameter less than or equal to 1 μm.

15. The device according to claim 1, wherein the well is formed as a depression in a plate of electrically insulating material.

16. The device according to claim 1 wherein the dimensions of the well are configured to keep a Johnson noise produced during measurement under a predetermined amount, the amount determined upon a desired solution of a signal measured from the well.

17. The device according to claim 1 wherein the dimensions of the well are configured to keep the signal to noise ratio at least 10 to 1.

18. The device according to claim 1 wherein the dimensions of the well are configured based on the current noise and bandwidth of a frequency.

* * * * *